United States Patent [19]

Fujiwara et al.

[11] Patent Number: 5,541,108
[45] Date of Patent: Jul. 30, 1996

[54] *GLUCONOBACTER OXYDANS* STRAINS

[75] Inventors: Akiko Fujiwara, Kamakura; Teruhide Sugisawa; Masako Shinjoh, both of Yokohama; Yutaka Setoguchi; Tatsuo Hoshino, both of Kamakura, all of Japan

[73] Assignee: Hoffmann-La Roche Inc., Nutley, N.J.

[21] Appl. No.: 266,998

[22] Filed: Jun. 28, 1994

Related U.S. Application Data

[63] Continuation of Ser. No. 183,924, Jan. 18, 1994, abandoned, which is a continuation of Ser. No. 16,478, Feb. 10, 1993, abandoned, which is a continuation of Ser. No. 517,972, Apr. 30, 1990, abandoned, which is a continuation of Ser. No. 899,586, Aug. 25, 1986, abandoned.

[30] Foreign Application Priority Data

Aug. 28, 1985 [GB] United Kingdom .................... 8521359
Jul. 22, 1986 [GB] United Kingdom .................... 8617888

[51] Int. Cl.$^6$ ................................ C12N 1/20; C12P 7/60
[52] U.S. Cl. .................. 435/252.1; 435/138; 435/172.1; 435/822; 435/170; 435/189
[58] Field of Search ................................ 435/252.1, 138, 435/822, 170, 189, 172.1

[56] References Cited

U.S. PATENT DOCUMENTS

| Re 34,851 | 2/1995 | Manning | 435/252.32 |
|---|---|---|---|
| 3,043,749 | 7/1962 | Huang | 195/47 |
| 3,234,105 | 2/1966 | Motizuki | 435/138 |
| 3,907,639 | 9/1975 | Makover | 195/36 |
| 5,082,785 | 1/1992 | Manning et al. | 435/252.32 |

FOREIGN PATENT DOCUMENTS 994119  9/1963  United Kingdom .................... 435/138

OTHER PUBLICATIONS

Stanbury et al. Principles of fermentation Technology, 1984, Pergamon Press.
ATCC Catalogue of Bacteria, 1989, p. 106.
Tsukada et al, Biotechnology and Bioengineering, vol 14, 1972 pp. 799–810, John Wiley & Sons, Inc.
Makover, et al., Biotechnology and Bioengineering XVII, pp. 1485–1514 (1975).
Isono, et al. Agr. Biol. Chem, 35 No. 4 pp. 424–431 (1968).
Okazaki, et al, Agr. Biol. Chem 32 No. 10 pp. 1250–1255 (1968).
Martin et al, Eur. S. Appl. Microbiology 3, pp. 91–95 (1976).
Acta Microbologica Sinica 20 (3): 246–251 (1980) (Abstract only).
Acta Microbiologica Sinica 21 (2): 185–191– (1981) (Abstract only).

*Primary Examiner*—Irene Marx
*Attorney, Agent, or Firm*—George M. Gould; William H. Epstein; Catherine A. Picut

[57] ABSTRACT

A process for producing 2-keto-L-gulonic acid which comprises converting L-sorbose and/or D-sorbitol into 2-keto-L-gulonic acid with the aid of a microorganism or its cell free extract, said microorganism belonging to the species *Gluconobacter oxydans* capable of producing 2-keto-L-gulonic acid and having L-sorbose dehydrogenase activity. Also disclosed are specific microorganisms useful in such process.

10 Claims, No Drawings

GLUCONOBACTER OXYDANS STRAINS

This is a continuation of application Ser. No. 08/183,924 filed Jan. 18, 1994, now abandoned which is a continuation of Ser. No. 08/016,478, filed Feb. 10, 1993 now abandoned, which is a continuation of Ser. No. 07/517,972 filed Apr. 30, 1990 now abandoned which is a continuation of Ser. No. 06/899,586 filed Aug. 25, 1986 now abandoned.

BACKGROUND OF THE INVENTION

It has been known that 2-keto-L-gulonic acid can be produced biosynthetically from D-sorbitol or L-sorbose. For example, in Japanese patent Publication No. 40,154/1976, it is reported that 2-keto-L-gulonic acid can be produced from D-sorbitol with the aid of microorganisms belonging to the genus Acetobacter, Bacterium or Pseudomonas which are capable of oxidizing the hydroxymethyl radical at the 1-position and the hydroxymethylene radical at the 2-position of D-sorbitol to convert those radicals into a carboxyl radical and a carbonyl radical, respectively, under aerobic conditions. However, according to the said process, the yield of 2-keto-L-gulonic acid is less than 6 g/l. Moreover, in "Acta Microbiologica Sinica" 21 (2) 185–191 (1981), it is reported that 2-keto-L-gulonic acid can be accumulated in a mixed culture broth of two microorganisms, i.e. *Pseudomonas striata* and *Gluconobacter oxydans* at the concentration of 30 and 37 g/l starting from 70 g/l and 100 g/l, respectively, of L-sorbose. However, it is reported that *Gluconobacter oxydans* alone produced trace amount of 2-keto-L-gulonic acid and *Pseudomonas striata* produced none at all.

SUMMARY OF THE INVENTION

The present invention relates to a process for producing 2-keto-L-gulonic acid by fermentation with a high yield, and to 2-keto-L-gulonic acid producing microorganisms.

2-keto-L-gulonic acid is an important intermediate foe the production of vitamin C and can be converted into vitamin C by a one-step chemical reaction according to known processes in the art.

DETAILED DESCRIPTION

The process provided by the present invention renders possible the production of 2-keto-L-gulonic acid from L-sorbose and/or D-sorbitol in high yield. This process comprises cultivating a microorganism belonging to the species *Gluconobacter oxydans* to convert L-sorbose and/or D-sorbitol into 2-keto-L-gulonic acid in a medium, the yield of 2-keto-L-gulonic acid being more than 20 g/l (e.g. more than 60 g/l under appropriate conditions) and the concentration of the substrate being in a range between 30–200 g/l , and if desired, recovering 2-keto-L-gulonic acid from the fermentation broth.

The microorganisms used in the process of this invention are those belonging to the species *Gluconobacter oxydans* or mutants thereof, which have L-sorbose dehydrogenase activity so as to be able to convert L-sorbose into L-sorbosone. Any microorganism of the species *Gluconobacter oxydans* or mutants thereof which have L-sorbose dehydrogenase activity can be utilized in the process of this invention. Among the preferred microorganisms are those having L-sorbose dehydrogenase activity of 20 m units/mg cell protein and higher and most preferably those having L-sorbose dehydrogenase activity of 50 m units/mg cell protein or higher. The microorganisms having such a high L-sorbose dehydrogenase activity can produce 2-keto-L-gulonic acid with a high yield, e.g. more than 60 g/l. The L-sorbose dehydrogenase activity can be measured by the DCIP (2,6-dichlorophenolindophenol)-assay described in K. Matsushita et al. "Method in Enzymology", Vol. 89, edited by W.A. Wood, Academic Press Inc., New York, N.Y., 1982, p. 187. One unit is defined as the amount of enzyme that catalyzed the reduction of 1 μmol of DCIP per minute under the standard assay conditions.

Although various different species had been known in the Gluconobacter genus, such as *Gluconobacter cerinus, Gluconobacter dioxyacetonicus, Gluconobacter industrius, Gluconobacter liquefaciens, Gluconobacter melanogenes, Gluconobacter oxydans, Gluconobacter suboxydans* and the like, all of those strains were classified in one species of *Gluconobacter oxydans* with 4 subspecies in the 8th Edition of "Bergey's Manual of Determinative Bacteriology" 1974), i.e. *oxydans, industrius, suboxydans* and *melanogenes*. Further, the new "Bergey's Manual of Systematic Bacteriology", Vol. I (1984) adopted the concept of the single species within the genus without subdividing into various subspecies. This was based on the numerical analysis of various strains and because subspecies cannot be regarded as biological entities.

Thus, according to the newest classification, all the strains belonging to Gluconobacter fall into the species *Gluconobacter oxydans*. Morphological and physiological characteristics of the strains belonging to *Gluconobacter oxydans* are described in "Bergey's Manual of Systematic Bacteriology", Vol. I, p. 275–278, 1984 and F. Gossele et al., International J. System. Bacteriol. Vol. 33, p. 65–81, 1983.

The mutants used in the present invention can be obtained by treating a wild type strain with a mutagen such as ultraviolet irradiation, X-ray irradiation, γ-ray irradiation or contact with nitrous acid or other suitable mutagens, or by isolating a clone occurring by spontaneous mutation. These mutations of a wild type strain or a mutant strain thereof may be effected in any of the ways per se well known for the purpose by one skilled in the art. Many of these methods have been described in various publications, for example, "Chemical Mutagens" edited by Y. Tajima, T. Yoshida and T. Kada, published by Kodansha Scientific Inc., Tokyo, Japan, in 1973.

Any strains belonging to the species *Gluconobacter oxydans* isolated from natural sources or publicly available from the collections may be employed as a parent strain for mutagenesis described in the present invention.

The mutants according to the present invention can also be obtained by fusion of the strains belonging to the species *Gluconobacter oxydans* and the combination of the mutagenesis and/or fusion. Such procedures are exemplified in the following Example 1.

The microorganisms preferably used in the present invention are *Gluconobacter oxydans* UV-10, *Gluconobacter oxydans* E-1, *Gluconobacter oxydans* H-2, *Gluconobacter oxydans* L-8, *Gluconobacter oxydans* U-13 or *Gluconobacter oxydans* Z-29 derived from the strains *Gluconobacter oxydans* (listed as melanogenes in the catalogue) IFO-3293 (FERM-P No. 8356). Those mutant strains have been deposited in the Agency of Industrial Science and Technology, Fermentation Research Institute, Japan under the following deposited Nos., respectively.

| | |
|---|---|
| *Gluconobacter oxydans* UV-10 | FERM-P No. 8422 |
| *Gluconobacter oxydans* E-1 | FERM-P No. 8353 |

| | |
|---|---|
| Gluconobacter oxydans H-2 | FERM-P No. 8354 |
| Gluconobacter oxydans L-8 | FERM-P No. 8355 |
| Gluconobacter oxydans U-13 | FERM-P No. 8854 |
| Gluconobacter oxydans Z-29 | FERM-P No. 8855 |

The morphology of these mutant strains is indistinguishable from that of the parent strains IFO-3293 (FERM-P No. 8356), but the former strains and the latter parent strain are clearly distinguishable in the production of 2-keto-gulonic acid and the L-sorbose dehydrogenase activity as described in the Examples.

The invention also includes the use of functionally equivalent mutants, variants and subcultures thereof. By functionally equivalent it is meant that the said microorganism has L-sorbose dehydrogenase activity and produces 2-keto-L-gulonic acid at a concentration of 20 g/L or more.

The production of 2-keto-L-gulonic acid is effected by the cultivation of a 2-keto-L-gulonic acid producing microorganism in a medium containing L-sorbose and/or D-sorbitol as well as appropriate nutrients. The process of this invention may also be carried out by culturing the microorganism and, after culturing, bringing the whole cell or the cell free extract collected from the culture into contact with L-sorbose and/or D-sorbitol. The cultivation procedure may be carried out in accordance with this invention according to conventional procedures utilizing a conventional nutrient medium.

In the case where the microorganism is cultured in a medium containing L-sorbose and/or D-sorbitol as well appropriate nutrients, the microorganism may be cultured in an aqueous medium under aerobic fermentation. The cultivation should be conducted at a pH of about 4.0 to about 8.0, preferably from about 4.5 to 6.5. A preferred temperature range for carrying out the cultivation is from about 20° C. to 37° C., preferably from 25° C. to 33° C. While the time for cultivation varies depending upon the microorganisms and nutrient medium to be used, about 2 to 10 days of cultivation usually brings about the most preferable results. Concentration of L-sorbose and/or D-sorbitol in the medium is generally desirable to be about 30 to 200 g/l, most preferably from about 50 to 150 g/l.

It is usually required that the culture medium contains such conventional nutrients for the microorganism as assimilable carbon sources, digestible nitrogen sources and preferably inorganic substances, vitamins, trace elements and other growth promoting factors. L-Sorbose and/or D-sorbitol per se can serve as the carbon source but other substances, which are carbon sources, may also be added. Among the substances which can be utilized as carbon sources, other than L-sorbose and D-sorbitol, are included, for example, glycerol, mannitol, fructose, D-arabitol and the like.

As the nitrogen sources, there may be used various organic or inorganic substances such as yeast extract, meat extract, peptone, casein, corn steep liquor, urea, amino acids, nitrates, ammonium salts, and the like. As the inorganic nutrients, for example, potassium phosphates, magnesium sulfate, ferrous and ferric chlorides, calcium carbonate and the like are usually employed.

In the case of using the whole cells collected from the culture, cultivation of the microorganism is carried out under similar conditions as described above. The whole cells are utilized to convert L-sorbose and/or D-sorbitol to 2-keto-L-gulonic acid in an aqueous medium under aerobic conditions at a pH of about 5 to 8. In this conversion, no additional nutrients are necessary. Generally, from about 1 to 4 days culture is preferable for obtaining the most effective cells for the conversion of L-sorbose and/or D-sorbitol to 2-keto-L-gulonic acid.

On the other hand, when cell free extracts from the whole culture are utilized, these cell free extracts can be used to convert L-sorbose and/or D-sorbitol to 2-keto-1-gulonic acid by treating the substrate with the cell free extracts in an aqueous medium under aerobic conditions at pH of 5 to 9. In this case, no nutrients need be present.

In the method of the present invention, the resulting 2-keto-L-gulonic acid in the reaction mixture need not be isolated, but the reaction mixture can directly be esterified, followed by enolization and lactonization and can be converted to L-ascorbic acid. In the case of isolating 2-keto-L-gulonic acid, isolation may be effected by the formation of a salt or by using differences in properties between the product and impurities such as solubility, adsorbability and distribution coefficient between two solvents. Use of an adsorbent such as ion exchange resins is one of the most convenient processes for isolation of the product. 2-keto-L-gulonic acid thus obtained is in general not pure and may be purified by conventional methods such as recrystallization and chromatography.

The following Examples illustrate the present invention.

EXAMPLE 1

An agar slant culture of *Gluconobacter oxydans* (listed in the catalogue as *melanogenes*) IFO-3293 (FERM-P No. 8356) was inoculated into 5 ml of a medium containing (%): glycerol, 0.5; yeast extract, 0.5; and $MgSO_4 \cdot 7H_2O$, 0.25 in a test tube and cultivated at 27° C. for 24 hours on a tube shaker. The cells were collected by centrifugation, washed twice with 50 mM tris-maleic acid buffer, pH 6.0, and suspended in 25 ml of the same buffer. A glass plate containing 2 ml of the cell suspension was kept under a UV light (254 nm, 15W) at a distance of 30 cm. After one minute of irradiation, the plate was taken out and kept in dark for 60 minutes before being spread on agar plates containing 5% L-sorbose and 1% $CaCO_3$. The colonies having large clear zones derived from dissolution of $CaCO_3$ were transferred onto agar plates and used to inoculate test tubes (21 mm in diameter) containing fermentation medium. The medium was composed of (g/l): L-sorbose, 70; yeast extract, 7.5; glycerol 0.5; $MgSO_4 \cdot 7H_2O$, 2.5 and $CaCO_3$, 10. After cultivation at 30° C. for 4 days, the culture was analyzed on tlc to quantify 2-keto-L-gulonic acid production. The strain UV-10 (FERM-P No. 8422) was selected as a high producer of 2-keto-L-gulonic acid.

UV-10 cells were treated with 125 μg/ml of N-methyl-N'-nitro-N-nitrosoguanidine (MNNG) and 62.5 μg/ml of acridine orange for 30 minutes at 30° C. in 0.05M phosphate buffer (pH, 8.0). The mutated cells were spread on No. 4 agar plates and grown. No. 4 medium contained 0.5% each of yeast extract, glycerol and $MgSO_4 \cdot 7H_2O$. From these mutants, the strain 56-8 was selected as a 2-keto-L-gulonic acid high producer.

By the repetition of the same mutational procedure as described above, the mutants s66-23 and s14-23 were obtained from the strain 56-8 as 2-keto-L-gulonic acid high producers. Moreover, by repeating the same procedure, using the strain s66-23 as a parent, the strain A-6 was selected as a 2-keto-L-gulonic acid high producer.

The fusion of the strains A-6 and s14-23 was carried out with the following procedure.

The strains A-6 and s14-23 were cultivated in 500 ml-Erlenmeyer flasks at 30° C. for 48 hours. The cells were collected from 10 ml of the culture broth by centrifugation, washed with water and suspended in 4.5 ml of the buffer containing 20 mMMgCl$_2$•6H$_2$O, 20 mM CaCl$_2$•2H$_2$O, 0.1M Tris, 1 mM EDTA and 0.5M NaCl (pH 8.0) and treated with lysozyme at 33° C. for 2.5 hours with gentle shaking. Spheroplast suspension was washed, resuspended in hypertonic medium and used for fusion.

1 ml each of the spheroplast suspension of A-6 and s14-23 was mixed and centrifuged at 2500 rpm for 10 minutes and resuspended in hypertonic medium. One ml of polyethylene glycol PEG-1000 (44%) was added to 0.1 ml of the spheroplast mixture and the mixture was incubated at 20° C. for 10 minutes.

Fused suspension was plated on hypertonic agar medium after an appropriate dilution. After incubation at 27.5° C. for about 6 days, colonies appeared on plates by regeneration. Fusants were selected from these colonies and cultured in test tubes to determine 2-keto-L-gulonic acid productivity. A 2-keto-L-gulonic acid high producer was selected among the fusants.

The fusant selected was further treated with MNNG in the same manner as described above and the strain E-1 (FERM-P No. 8353) was obtained as a high 2-keto-L-gulonic acid producer. The 2-keto-L-gulonic acid high producers, H-2 (FERM-P No. 8354) and L-8 (FERM-P No. 8355) were obtained by further mutation of the strains E-1 (FERM-P No. 8353) and H-2 (FERM-P No. 8354) respectively as parents.

By the repetitive mutagenesis of the strain H-2 (FERM-P No. 8354) and its derivatives using 2-methoxy-6-chloro-9-[3-(ethyl-2-chloroethyl)aminopropylamino]acridine-dihydrochloride (ICR-170) or MNNG as mutagens in the same manner as described above, the strain U-13 (FERM-P No. 8854) was selected as a 2-keto-L-gulonic acid high producer. Furthermore, by the repetitive mutagenesis of the strain H-2 (FERM-P No. 8354) and its derivatives using ICR-170,MNNG and/or 2-methoxy-6-chloro-913-(2-chloroethyl)aminopropylamino]acridine-dihydro-chloride (ICR-191) as mutagens in the same manner as described above, the strain Z-29 (FERM-P No. 8855) was selected as a 2-keto-L-gulonic acid high producer.

EXAMPLE 2

Agar slant cultures of Gluconobacter strains listed below were inoculated into 5 ml of a medium in test tubes, said medium containing (g/l): L-sorbose, 80; glycerol, 0.5; MgSO$_4$•7H$_2$O, 0.25; yeast extract (Oriental Yeast Co.), 15; and CaCO$_3$, 15.0. They were grown for 48 hours at 30° C. on a test tube shaker. 1 ml of the resulting culture was used to inoculate 50 ml of fresh medium in a 500 ml-Erlenmeyer flask. Composition of the medium was the same as described above. The flasks were incubated at 30° C. on a rotary shaker operating at 180 rpm for 4 days. The amount of 2-keto-L-gulonic acid accumulated in the culture was as follows.

|  | 2-keto-L-gulonic acid yield (g/l) | |
| --- | --- | --- |
| Strains | after 3 days | after 4 days |
| G. oxydans IFO-3293 | 0.4 | 0.5 |
| G. oxydans UV-10 | 23.9 | 27.8 |
| G. oxydans E-1 | 46.5 | 49.2 |
| G. oxydans H-2 | 47.2 | 50.0 |
| G. oxydans L-8 | 46.3 | 46.5 |

EXAMPLE 3

Gluconobacter oxydans E-1 (FERM-P No. 8353), H-2 (FERM-P No. 8354) and L-8 (FERM-P No. 8355) were cultivated in a similar manner as described in Example 2. L-Sorbose concentrations of 80 g, 100 g and 120 g/l and CaCO$_3$ concentrations of 15 g, 20 g and 30 g/l, respectively, were used in the production medium. Fermentation was performed for 5 days and a sample was withdrawn from each flask on the third day of cultivation. The yields of 2-keto-L-gulonic acid in the medium as expressed in grams per liter are summarized in the following table.

| L-Sorbose | culture | Strain | | |
| --- | --- | --- | --- | --- |
| concentration | period | E-1 | H-2 | L-8 |
| 80 g/l | 3 day | 46.1 | 50.5 | 48.2 |
|  | 5 day | 46.3 | 49.3 | 48.1 |
| 100 g/l | 3 day | 51.4 | 57.3 | 58.3 |
|  | 5 day | 55.1 | 62.8 | 61.9 |
| 120 g/l | 3 day | — | 64.2 | 62.2 |
|  | 5 day | — | 65.0 | 67.8 |

Using Gluconobacter oxydans IFO 3293 (FERM-P No. 8356), the same procedure as mentioned above was repeated, however less than 1 g/l of 2-keto-L-gulonic acid was only detected.

EXAMPLE 4

Gluconobacter oxydans L-8 (FERM-P No. 8355) was cultivated in the same manner as described in Example 2 in the media containing the following ingredients (g/l):

|  | (A) | (B) | (C) | (D) |
| --- | --- | --- | --- | --- |
| D-Sorbitol | 120 | 100 | 80 | 43 |
| L-Sorbose | — | — | — | 57 |
| Glycerol | 0.5 | 0.5 | 0.5 | 0.5 |
| MgSO$_4$.7H$_2$O | 2.5 | 2.5 | 2.5 | 2.5 |
| Yeast extract | 15.0 | 15.0 | 15.0 | 15.0 |
| CaCO$_3$ | 30 | 20 | 15 | 20 |

The flasks were incubated at 30° C. for 4 days on a rotary shaker. Amounts of 2-keto-L-gulonic acid accumulated in the medium (A) to (D) were 58.1, 51.3, 40.8 and 46.5, g/l, respectively.

EXAMPLE 5

Gluconobacter oxydans U-13 (FERM-P No. 8854) and Z-29 (FERM-P No. 8855) were cultured in the same manner as described in Example 2 in the media containing the following ingredients (g/L):

| Ingredients | Medium | | |
| --- | --- | --- | --- |
| (g/L) | (A) | (B) | (C) |
| L-Sorbose | 100 | — | — |
| D-Sorbitol | — | 100 | 100 |
| Glycerol | 0.5 | 0.5 | 0.5 |
| MgSO$_4$.7H$_2$O | 2.5 | 2.5 | 2.5 |
| Yeast extract | 15.0 | 15.0 | — |
| Corn steep liquor | — | — | 20.0 |
| CaCO$_3$ | 20.0 | 20.0 | 20.0 |

The flasks were incubated at 30° C. for 4 days on a rotary shaker. The amount of 2-keto-L-gulonic acid accumulated in the culture was as follows.

| Strains | 2-Keto-L-gulonic acid (g/L) in Medium | | |
|---|---|---|---|
| | (A) | (B) | (C) |
| G. oxydans U-13 | 64.4 | 45.9 | — |
| G. oxydans Z-29 | — | 62.5 | 59.5 |

EXAMPLE 6

One loopful of cells of *Gluconobacter oxydans* L-8 (FERM-P No. 8355) was inoculated into a test tube containing 5 ml of the following medium.

| L-Sorbose | 80.0 g/l |
|---|---|
| Glycerol | 0.5 |
| $MgSO_4.7H_2O$ | 2.5 |
| Yeast extract | 15.0 |
| $CaCO_3$ | 15.0 |

After incubation at 30° C. for 2 days on a test tube shaker, 1 ml of the culture was transferred to six 500 ml-Erlenmeyer flasks each containing 50 ml of the above medium but L-sorbose concentration was 100 g/l.

The flasks were incubated at 30° C. with rotary shaking for 2 days, whereupon the cultures obtained served as inoculum. 300 ml of the incubated inoculum was added to 15 l of the medium in a fermentor having a total volume of 30 l. The medium contained (g/l): L-sorbose, 100; glycerol, 0.5; $MgSO_4 \omega 7H_2O$, 2.5; yeast extract, 15 and $CaCO_3$, 20. Incubation was conducted at 30° C. with stirring at a rate of 300 rpm and with an aeration rate of 8 l/min. 2-Keto-L-gulonic acid content in the fermented broth was 55.4 g/l after 87 hours.

Cells and solid materials in the broth were discarded by centrifugation and 14 l of clear supernatant was obtained. The supernatant was passed over IR12B($H^+$) resin. The passed fraction was then adsorbed on Dowex 44 ($OH^-$) resin and eluted with 0.5% ammonium hydroxide. The eluate was passed through IR120B($Na^+$) resin. The passed fraction was concentrated to 3 l under reduced pressure. 1.5 l of ethanol was added to the concentrate and the solution was kept standing at 5° C. 550 g of crystals of sodium 2-keto-L-gulonic acid monohydrate were obtained. The crystalline product showed identical physicochemical characteristics with an authentic sample: melting point, 144° C.

EXAMPLE 7

*Gluconobacter oxydans* E-1 (FERM-P No. 8353) was cultivated in two 500 ml-Erlenmeyer flasks each containing 50 ml of the medium in the same manner as described in Example 2. The cells were collected after 3 days of cultivation, washed twice with saline solution and suspended in 50 ml of 0.3% NaCl containing 50 g/l of L-sorbose. 32 g/l of 2-keto-L-gulonic acid accumulated in the mixture after 3 days incubation at 30° C.

EXAMPLE 8

*Gluconobacter oxydans* L-8 (FERM-P No. 8355) was cultivated in a 30 l jar fermentor in the same manner as described in Example 5. After 38 hours of cultivation, 1.5 l of the culture was harvested to obtain the cells. 10 g of the cells were suspended into 60 ml of 10 mM potassium phosphate buffer (pH, 7.0) and homogenized by a Dyno mill homogenizer (Willy, A. Bachofen Co.) with glass beads at 2000 rpm for 4 minutes at 4° C. The homogenate was centrifuged at 5000 rpm for 10 minutes to remove the intact cells. 2 ml of the supernatant thus obtained was mixed with 1 ml of 0.5M potassium phosphate buffer (pH, 7.0) and 6 ml of water containing 100 mg of L-sorbose and incubated at 30° C. for 4 hours. As a result, 25 mg of 2-keto-L-gulonic acid was formed.

EXAMPLE 9

The strains *Gluconobacter oxydans* IFO-3293 (FERM-P UV-10 (FERM-P 8422), E-1 (FERM-P 8353), H-2 (FERM-P and L-8 (FERM-P 8355) were cultivated in 30 l fermentors for 38 hours and the cell free extracts of the cultures were prepared in a manner analogous to that of Example 8. Activity of L-sorbose dehydrogenase was assayed. The results are shown in the following Table.

| Strains | L-Sorbose dehydrogenase activity (m unit/mg protein) |
|---|---|
| *G. oxydans* | |
| IFO 3293 | <1 |
| UV-10 | 55 |
| E-1 | 70 |
| H-2 | 78 |
| L-8 | 84 |

We claim:

1. A biologically pure culture of a microorganism of the species *Gluconobacter oxydans* which microorganism has L-sorbose dehydrogenase enzyme activity of at least 20 m units/mg cell protein for converting L-sorbose to L-sorbosone.

2. The microorganism of claim 1, wherein said microorganism produces 2-keto-L-gulonic acid at a concentration greater than 20 g/l from D-sorbitol and/or L-sorbose in a fermentation medium.

3. The microorganism of claim 1, wherein said microorganism has an L-sorbose dehydrogenase activity of at least 50 m units/mg cell protein.

4. The microorganism of claim 2, wherein said microorganism produces 2-keto-L-gulonic acid at a concentration greater than 60 g/l from D-sorbitol and/or L-sorbose in a fermentation medium.

5. The microorganism of claim 2, wherein said microorganism is *Gluconobacter oxydans* UV-10, FERM BP-1267, or any mutant, thereof, wherein said mutant, has L-sorbose dehydrogenase enzyme activity of at least 20 m units/mg cell protein.

6. The microorganism of claim 2, wherein said microorganism is *Gluconobacter oxydans* Z-29, FERM BP-1270, or any mutant, thereof, wherein said mutant, has L-sorbose dehydrogenase enzyme activity of at least 20 m units/mg cell protein.

7. The microorganism of claim 2, wherein said microorganism is *Gluconobacter oxydans* E-1, FERM BP-1265, or any mutant, wherein said mutant, has L-sorbose dehydrogenase enzyme activity of at least 20 m units/mg cell protein.

8. The microorganism of claim 2, wherein said microorganism is *Gluconobacter oxydans* U-13, FERM BP-1269, or any mutant, thereof, wherein said mutant, has L-sorbose dehydrogenase enzyme activity of at least 20 m units/mg cell protein.

9. The microorganism of claim 2, wherein said microorganism is *Gluconobacter oxydans* H-2, FERM BP-1266, or any mutant, thereof, wherein said mutant, has L-sorbose dehydrogenase enzyme activity of at least 20 m units/mg cell protein.

10. The microorganism of claim 2, wherein said microorganism is *Gluconobacter oxydans* L-8, FERM BP-1268, or any mutant, thereof, wherein said mutant, has L-sorbose dehydrogenase enzyme activity of at least 20 m units/mg cell protein.

\* \* \* \* \*